(12) United States Patent
Chiou et al.

(10) Patent No.: US 10,415,084 B2
(45) Date of Patent: Sep. 17, 2019

(54) MULTIPLEX SLIDE PLATE DEVICE AND OPERATION METHOD THEREOF

(71) Applicant: Quark Biosciences Taiwan, Inc., Hsinchu County (TW)

(72) Inventors: Chung-Fan Chiou, Hsinchu County (TW); Cheng-Wey Wei, Hsinchu County (TW); Yu Chang, Hsinchu County (TW); Ming-Chuan Hsu, Hsinchu County (TW)

(73) Assignee: Quark Biosciences Taiwan, Inc., Hsinchu County (TW)

( * ) Notice: Subject to any disclaimer, the term of this patent is extended or adjusted under 35 U.S.C. 154(b) by 501 days.

(21) Appl. No.: 15/149,185

(22) Filed: May 9, 2016

(65) Prior Publication Data

US 2016/0251701 A1    Sep. 1, 2016

Related U.S. Application Data

(63) Continuation-in-part of application No. 13/928,396, filed on Jun. 27, 2013, now Pat. No. 9,724,692.

(30) Foreign Application Priority Data

Mar. 1, 2016 (TW) .............................. 105106095 A

(51) Int. Cl.
*B01L 3/00* (2006.01)
*C12Q 1/686* (2018.01)

(52) U.S. Cl.
CPC .......... *C12Q 1/686* (2013.01); *B01L 3/50851* (2013.01); *B01L 3/502738* (2013.01);
(Continued)

(58) Field of Classification Search
None
See application file for complete search history.

(56) References Cited

U.S. PATENT DOCUMENTS

| 4,970,053 A | 11/1990 | Fechtner |
| 5,710,381 A | 1/1998 | Atwood et al. |

(Continued)

FOREIGN PATENT DOCUMENTS

| CN | 101631502 | 1/2010 |
| CN | 101896275 | 11/2010 |

(Continued)

OTHER PUBLICATIONS

Kim et al., A Disposable, Self-Contained PCR Chip, Lab Chip. Feb. 21, 2009; 9(4): 606-612. Published online Nov. 18, 2008.*

(Continued)

*Primary Examiner* — Aaron A Priest
(74) *Attorney, Agent, or Firm* — JCIPRNET

(57) ABSTRACT

A multiplex slide plate device and an operation method thereof are provided. The multiplex slide plate device includes a slide plate and a sacrificial layer. The slide plate has reaction vessels arranged in an array, wherein each of the reaction vessels has an opening portion and a bottom portion. The sacrificial layer has a microfluidic channel, wherein the microfluidic channel has an injection channel, a main channel and a distal channel connected to each other. The sacrificial layer is assembled to the slide plate, wherein the main channel faces the opening portion. A sample solution is injected into the injection channel, such that the sample solution flows from the injection channel through the main channel to the distal channel, wherein the sample solution loads into each of the reaction vessels while flowing through the main channel.

5 Claims, 6 Drawing Sheets

(52) U.S. Cl.
CPC ............ *B01L 2200/0605* (2013.01); *B01L 2200/0673* (2013.01); *B01L 2200/16* (2013.01); *B01L 2300/02* (2013.01); *B01L 2300/041* (2013.01); *B01L 2300/0819* (2013.01); *B01L 2300/0858* (2013.01); *B01L 2300/0861* (2013.01); *B01L 2300/0864* (2013.01); *B01L 2300/18* (2013.01); *B01L 2400/0677* (2013.01)

(56) References Cited

U.S. PATENT DOCUMENTS

| | | |
|---|---|---|
| 5,985,218 A | 11/1999 | Goodale |
| 6,149,872 A | 11/2000 | Mack et al. |
| 6,716,629 B2 | 4/2004 | Hess et al. |
| 6,893,877 B2 | 5/2005 | Hunter et al. |
| 7,307,802 B2 | 12/2007 | Unger |
| 7,332,271 B2 | 2/2008 | O'Keefe et al. |
| 7,588,672 B2 | 9/2009 | Unger et al. |
| 7,614,135 B2 | 11/2009 | Santini, Jr. et al. |
| 7,666,360 B2 | 2/2010 | Schellenberger et al. |
| 7,682,565 B2 | 3/2010 | Linton et al. |
| 2003/0124716 A1 | 7/2003 | Hess et al. |
| 2004/0187951 A1 | 9/2004 | Barker |
| 2006/0000337 A1 | 1/2006 | Gass |
| 2007/0074972 A1 | 4/2007 | Nassef et al. |
| 2007/0202010 A1 | 8/2007 | Talebpour et al. |
| 2008/0108112 A1 | 5/2008 | O'keefe et al. |
| 2009/0117620 A1 | 5/2009 | Fritchie et al. |
| 2009/0246782 A1* | 10/2009 | Kelso ............ B01L 3/502761 435/6.16 |
| 2009/0294703 A1 | 12/2009 | Unger et al. |

FOREIGN PATENT DOCUMENTS

| | | |
|---|---|---|
| CN | 102027367 | 4/2011 |
| CN | 202968546 | 6/2013 |
| CN | 104250612 | 12/2014 |
| TW | 201500548 | 1/2015 |
| WO | 2005028629 | 3/2005 |

OTHER PUBLICATIONS

Leamon et al., "A massively parallel PicoTiterPlate based platform for discrete picoliter-scale polymerase chain reactions," Electrophoresis, Nov. 2003, pp. 3769-3777.

Yang Li, "Microwell Array Based Universal Multiplex PCR and Its Application," Dissertation submitted to Shanghai Jiao Tung University for the Degree of Master, Feb. 2011, pp. 1-70.

Hernan V. Fuentes et al., "Phase-Changing Sacrificial Layer Fabrication of Multilayer Polyer Microfluidic Devices," Anal Chem., 80(1): 333-339. doi: 10.1021/ac7017475, Jan. 1, 2008, pp. 1-14.

* cited by examiner

MULTIPLEX SLIDE PLATE DEVICE AND OPERATION METHOD THEREOF

CROSS-REFERENCE TO RELATED APPLICATIONS

This application is a continuation-in-part application of and claims the priority benefit of U.S. patent application Ser. No. 13/928,396, filed on Jun. 27, 2013, now pending. This application also claims the priority benefit of Taiwan application serial no. 105106095, filed on Mar. 1, 2016. The entirety of each of the above-mentioned patent applications is hereby incorporated by reference herein and made a part of this specification.

BACKGROUND OF THE INVENTION

1. Field of the Invention

The invention relates to a multiplex slide plate device for molecular biological detection and an operation method thereof, and more specifically, to a multiplex slide plate device prefilled with polymerase chain reaction (PCR) reagent(s) and an operation method thereof.

2. Description of Related Art

In the field of molecular biological detection, a multiplex test may be required to simultaneously measure multiple biomolecules of a biological sample in a single run/cycle of the test. For example, measuring several single-nucleotide polymorphism (SNP) genotypes, or the expression levels of a number of genes of a sample via polymerase chain reaction (PCR) assays. At this time, multiple DNA or RNA assays may compose a test panel. A PCR assay comprises at least two DNA specific primer probes (for some PCR assays also include additional target-specific reporter probes), and this pair of primers has to correctly mix with the DNA template extracted from the sample to be tested so as to measure the presence or the amount of the specific DNA targets in the sample.

Traditionally, the pair of primers and the sample are delivered to the same reaction vessel for PCR. The delivery is usually done by pipetting the solution from each vial which stores primer pairs, enzymes and reagents, and pipetting the sample, to the reaction vessel. The most common vessel format is the 96-well titter plate. In such way, a PCR assay requires at least two pipettings, one for adding the primer pairs and another one for adding the sample to the reaction vessel. For example, for a panel to examine 36 targets in one sample, it needs at least 36 pipettings to add each pair of primers to 36 different reaction vessels, and another 36 pipettings to add sample to each of the above reaction vessels. This part of operation method is not only complicated and error-prone, but also labor-intensive.

If the primer pairs are pre-filled in each of the reaction vessels, the PCR experiment operator only needs to add sample to the pre-filled vessels. The above mentioned example of detecting one sample for 36 targets would require only 36 pipettings for adding sample to 36 pre-filled vessels. Besides, the reaction vessel volume can be reduced to nano-liter range to save the amount of reaction reagents. The result format of 96-well titter plate, which is a common carrier vessel, is changed into a slide-like micro-titter plate by this improvement.

However, the size and volume of reaction vessels (also called micro-wells or nano-wells) in a micro-titer plate are too small to be filled with the primer pairs or samples manually without causing cross-contamination between neighbouring vessels (i.e. the primer pairs escape from one well to other wells). Therefore, the microfluidic technology or system for dispensing primer pairs or samples is required. In more detail, primer pairs are delivered to each of the nano-wells in advance and immobilized onto the inter-surfaces of the nano-well. Afterwards, the user can apply the sample to each of the reaction vessels by single pipetting operation or single microfluidic channel without worrying about primers escaping from one well to other wells, such that the cross-contamination between wells is minimized.

When the sample testing is performed subsequently, each reaction vessel must be filled with the predetermined amount of sample. The traditional method is to use pipette or needle dispensers to load the sample "one by one" into the reaction wells. However, as the volume of reaction vessel becomes smaller and the inter-well distance becomes closer, special mechanical system or paths may be needed for the dispenser to reach each reaction vessels individually, which is complicated and time-consuming. If adding sample into each of the reaction vessels by single pipetting operation or single microfluidic chaimel can be achieved by a special slide plate device, it is possible to greatly simplify the manual operation required in PCR reagent preparation, and enhance the convenience when sample filling.

SUMMARY OF THE INVENTION

The invention provides a multiplex slide plate device and an operation method thereof. The multiplex slide plate device and the operation method of the invention is for molecular biological detection, more specifically, for PCR, and even more specifically, for real-time PCR. The sample can be loaded into each reaction vessel of the slide plate quickly and uniformly through the multiplex slide plate device and the operation method of the invention, and all of the reaction vessels can be filled in an extremely short time by single pipetting.

The invention provides a multiplex slide plate device including a slide plate and a sacrificial layer. The slide plate has a plurality of reaction vessels, a first injection hole and a first exhaust hole. The reaction vessels are arranged in an array, wherein each of the reaction vessels has an opening portion and a bottom portion. The sacrificial layer has a microfluidic channel, wherein the microfluidic channel has an injection channel, a main channel and a distal channel connected to each other. The sacrificial layer is assembled to the slide plate, wherein the main channel faces the opening portion. A sample solution is injected from the first injection hole to the injection channel, such that the sample solution flows from the injection channel through the main channel to the distal channel, wherein the sample solution loads into each of the reaction vessels while flowing through the main channel.

In an embodiment of the invention, the multiplex slide plate device includes a housing which accommodates the slide plate and the sacrificial layer. The housing has a second injection hole and a second exhaust hole. The sample solution is injected from the second injection hole and the first injection hole to the injection channel, such that the sample solution flows from the injection channel through the main channel to the distal channel, wherein the sample solution loads into each of the reaction vessels while flowing through the main channel.

In an embodiment of the invention, the material of the housing includes a thermally conductive material.

In an embodiment of the invention, the housing includes an upper cover and a bottom plate, and the upper cover is assembled to the bottom plate, wherein the upper cover has a groove to accommodate the slide plate and the sacrificial layer, and the second injection hole and the second exhaust hole are located in the upper cover.

In an embodiment of the invention, the housing includes a label.

In an embodiment of the invention, the material of the slide plate includes a transparent material.

In an embodiment of the invention, the transparent material includes polycarbonate or polymethyl methacrylate (PMMA).

In an embodiment of the invention, the material of the sacrificial layer includes wax.

The invention provides a multiplex slide plate device including a slide plate and a sacrificial layer. The slide plate has a plurality of reaction vessels. The reaction vessels are arranged in an array, wherein each of the reaction vessels has an opening portion and a bottom portion. The sacrificial layer has a microfluidic channel, wherein the microfluidic channel has an injection channel, a main channel and a distal channel connected to each other. The sacrificial layer is assembled to the slide plate, wherein the main channel faces the opening portion. A sample solution is injected to the injection channel, such that the sample solution flows from the injection channel through the main channel to the distal channel, wherein the sample solution loads into each of the reaction vessels while flowing through the main channel.

In an embodiment of the invention, the multiplex slide plate device includes a housing which accommodates the slide plate and the sacrificial layer. The housing has an injection hole and an exhaust hole. The sample solution is injected from the injection hole to the injection channel, such that the sample solution flows from the injection channel through the main channel to the distal channel, wherein the sample solution loads into each of the reaction vessels while flowing through the main channel.

In an embodiment of the invention, the material of the housing comprises a thermally conductive material.

In an embodiment of the invention, the housing comprises an upper cover and a bottom plate, the upper cover is assembled to the bottom plate, and the upper cover has a groove to accommodate the slide plate and the sacrificial layer, the injection hole and the exhaust hole are located in the upper cover.

In an embodiment of the invention, the housing includes a label.

In an embodiment of the invention, the material of the slide plate includes a transparent material.

In an embodiment of the invention, the transparent material includes polycarbonate or PMMA.

In an embodiment of the invention, the material of the sacrificial layer includes wax.

The invention provides an operation method of a multiplex slide plate device including the following steps. First, a multiplex slide plate device including a slide plate, a sacrificial layer and a housing for accommodating the slide plate and the sacrificial layer is assembled. The slide plate has a plurality of reaction vessels arranged in an array, wherein each of the reaction vessels has an opening portion and a bottom portion. The sacrificial layer has a microfluidic channel, and the microfluidic channel has an injection channel, a main channel and a distal channel connected to each other, wherein the main channel faces the opening portion. Then, a sample solution is injected to the injection channel through an injection hole of the housing, such that the sample solution flows from the injection channel through the main channel to the distal channel, wherein the sample solution loads into each of the reaction vessels while flowing through the main channel. Afterwards, an oil is injected to the injection channel through the injection hole of the housing, such that the oil flows from the injection channel through the main channel to the distal channel, wherein the oil removes the sample solution which is not loaded into the reaction vessels while flowing through the main channel. Finally, the sacrificial layer is heated to melt, and the melted sacrificial layer is mixed with the oil.

In an embodiment of the invention, the oil includes mineral oil or silicone oil.

In an embodiment of the invention, the material of the housing comprises a thermally conductive material.

In an embodiment of the invention, the housing includes a label.

In an embodiment of the invention, the material of the slide plate includes a transparent material.

In an embodiment of the invention, the transparent material includes polycarbonate or PMMA.

In an embodiment of the invention, the material of the sacrificial layer includes wax.

Based on the above, the invention provides a multiplex slide plate device and an operation method thereof, such that the sample can be loaded into each reaction vessel of the slide plate quickly and uniformly while flowing through the main channel of the sacrificial layer, and then the sample solution which is not loaded in the reaction vessels is removed by the oil. Therefore, all of the reaction vessels can be filled in an extremely short time by single pipetting operation, so the experiment operation can be simplified with time-saving effect.

On the other hand, the distance between the slide plate and the sacrificial layer is at least about 10 μm, and the sacrificial layer has a certain thickness. In the PCR experiment process, the sacrificial layer is heated to melt, and the melted sacrificial layer mixes with the oil. Therefore, the distance between the slide plate and the bottom plate is about 600 μm, so the reaction can be performed successfully. A certain distance between the slide plate and the bottom plate can be maintained without adding an excess amount of sample, so it is able to save the input amount of sample.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

The invention provides a multiplex slide plate device and an operation method thereof, which can be widely applied to various types of reaction assays. The following descriptions are provided to further define the present invention for illustration purposes.

A reagent may refer to a formulation of several ingredients used for a particular test. For example, in the test using polymerase chain reaction (PCR), the testing reagent includes a pair of primers, enzymes, dNTPs, fluorescent reporters, salts and etc. During application, the different primer pairs and fluorescent reporters may be added to the reaction vessel firstly, and then followed by mixing the enzymes, dNTP, and other additives with the sample to the reaction vessel.

Sample(s) generally refers to the nucleic acid sample being tested. For example, the sample may be nucleic acid fragments (DNAs or RNAs) extracted from the blood, tissue or saliva.

Assay(s) or test(s) may refer to one or more assays or test items performed to the same sample. For example, using PCR to check a nucleic acid sample for 300 SNP assay, such assay includes a number of PCR test items by checking each genotype (A, T, C, G) of each SNP. For example, using real time PCR to determine amount of nucleic acid carrying a specific sequence.

Sample solution refers to the mixture or solution of the aforementioned sample mixed with master mix.

Reaction vessel may represent the tube, the individual tube(s) of the tube plate, the hole(s) or well(s) in the micro-titer plate, the individual reaction well(s) or pit(s) in the test slide plate or the array plate. As described herein, the "slide plate", "slide piece", "assay array plate" or "assay plate" may refer to the same substrate plate accommodating the reaction vessels.

When the volume of the liquid in the container is reduced to a certain level, the flow of the liquid in the container is dominated by surface adhesion, rather than gravity. If the volume of the liquid in the container is only a few nano-liters, the liquid has high surface adhesion to the container (nanowell), so that the liquid can be regarded as stable as an adhesive attached to the bottom or the wall of the container.

Preferably, the reaction vessel may be individual reaction well(s) or pit(s) in the test slide or the assay array plate. As discussed above, it is preferably to utilize the reaction vessel of a smaller volume, ranging from several to hundreds of nano-liters, for example.

Figure 1:
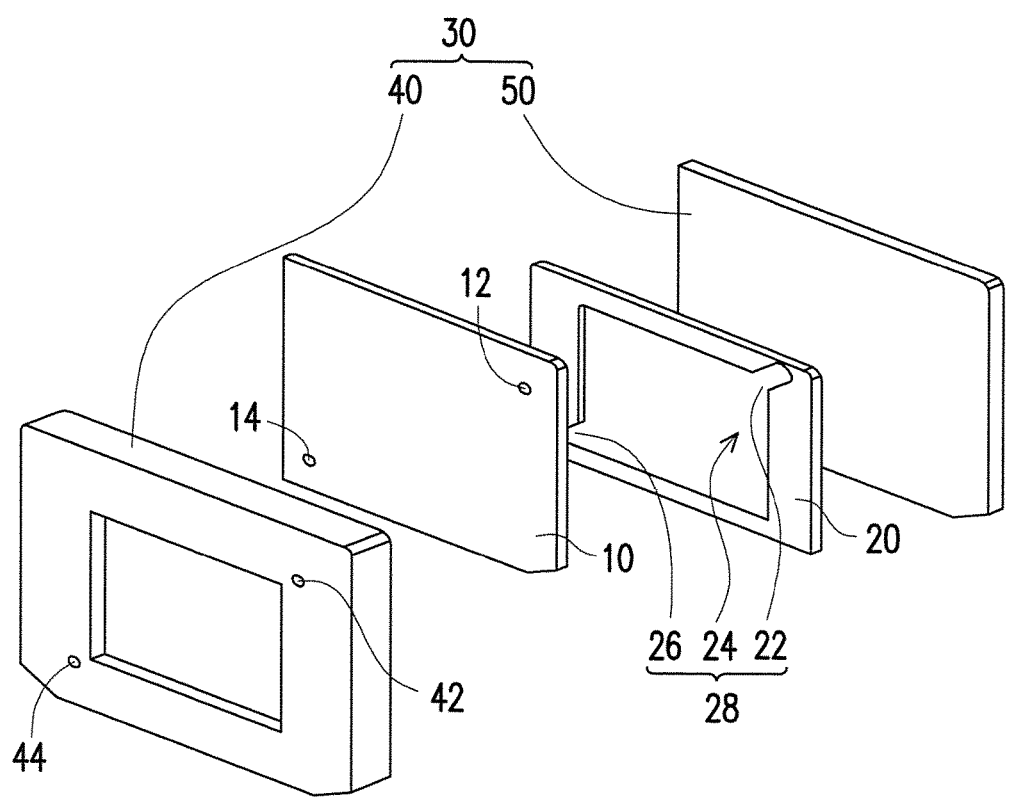
FIG. 1 is a schematic view illustrating a multiplex slide plate device according to the first embodiments of the invention.

FIG. 1 is a schematic view illustrating the structure of the multiplex slide plate device according to the first embodiments of the invention.

Referring to FIG. 1, a multiplex slide plate device includes a slide plate 10, a sacrificial layer 20 and a housing 30, wherein the housing 30 can be used to accommodate the slide plate 10 and the sacrificial layer 20. The structure of the slide plate 10 in FIG. 2 and FIG. 3 is illustrated in the following description.

Figure 2:
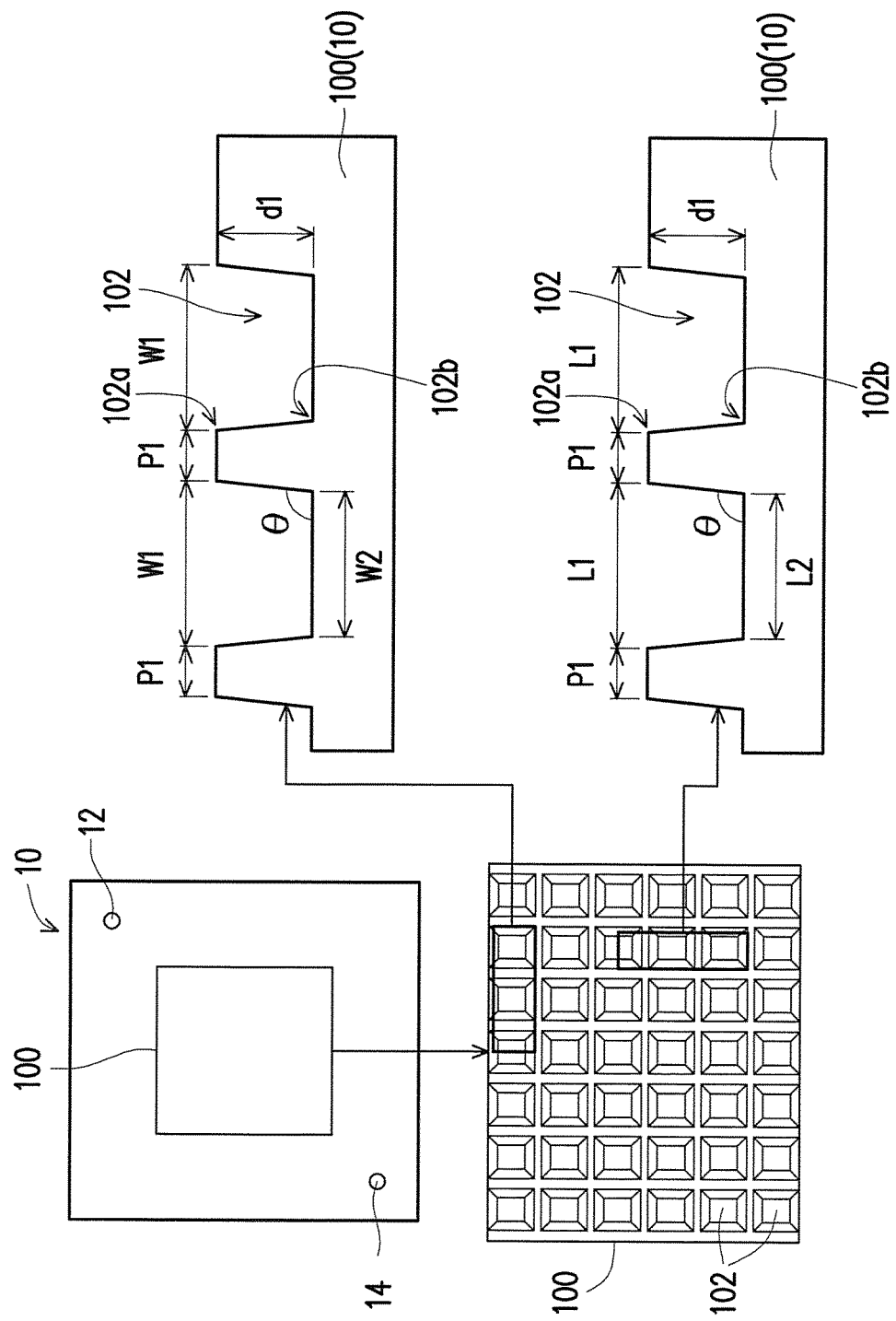
FIG. 2 is a schematic view illustrating a slide plate according to the first embodiments of the invention.
Figure 3:
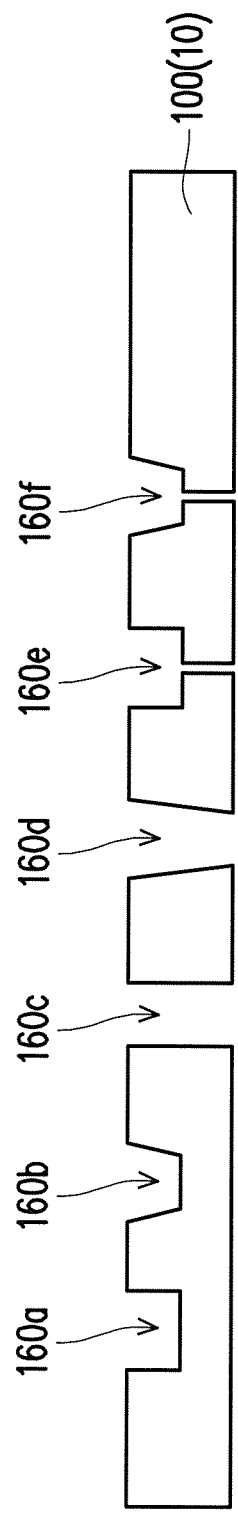
FIG. 3 is a schematic cross-sectional view of reaction vessels of a slide plate according to the first embodiments of the invention.

FIG. 2 is a schematic view illustrating a slide plate according to the first embodiments of the invention.

Referring to FIG. 2, the slide plate 10 has an assay region 100, and the area of the assay region 100 is 22.5 mm×22.5 mm. The assay region 100 includes a plurality of reaction vessels 102, wherein the reaction vessels 102 are arranged in an n×n array. Besides, the slide plate 10 further includes an injection hole 12 and an exhaust hole 14. In the present embodiment, the overall dimension of the slide plate 10 is 42 mm×36 mm×2 mm, for example. More specifically, the material of the slide plate 10 may include a transparent material, and the transparent material may be polycarbonate (PC) or polymethyl methacrylate (PMMA), for example.

Referring to FIG. 2, from the cross-sectional views (right part of FIG. 2) of the slide plate 10, each of the reaction vessels 102 may be wide in the opening portion 102a and narrower in the bottom portion 102b. In the present embodiment, each of the reaction vessels 102 has a depth of 100 μm (d1), with 200 μm (L1)×185 μm (W1) for the dimension of the opening portion 102a and 106.74 μm (L2)×91.74 μm (W2) for the dimension of the bottom portion 102b, for example. The pitch (p1) between the reaction vessels 102 may range from 25 μm~40 μm, and the slanted sidewall of the reaction vessels 102 may has an angle θ between 90 to 140 degrees, preferably between 100 to 135 degrees, more preferably 110 to 120 degrees, for example. Each of the reaction vessels 102 may accommodate 2.1 nano-liters of sample solution, for example.

FIG. 3 is a schematic cross-sectional view of reaction vessels of a slide plate according to the first embodiments of the invention.

Referring to FIG. 3, the reaction vessels of the slide plate 10 can be designed with different shapes or profiles. For example, the reaction vessels 160a and 160b are concave cavities formed within the slide plate 10 but not penetrating through the slide plate 10. The reaction vessels 160b, 160d and 160f have slanted sidewalls. The reaction vessels 160c, 160d, 160e and 160f penetrate through the slide plate 10 and have two open ends at the top and bottom surfaces of the slide plate 10. Due to the capillary action, the sample liquid is steadily hold in the reaction vessels 160c, 160d, 160e and 160f. The reaction vessel 160d penetrate through the slide plate 10 and has two open ends at the top and bottom surfaces of the slide plate 10, and has slanted sidewalls connecting the two open ends.

However, the structures in FIG. 2 and FIG. 3 are for illustration only, and the shape, size or number of the reaction vessels of the invention is not limited. The cross-sectional shape of the reaction vessels may be a circle, square or polygon, for example.

Generally, as the primers are soluble in aqueous solvents or solutions, the slide plate of the invention may be designed to be hydrophilic in the inner wall and the bottom surface of the reaction vessels, and to be hydrophobic in the regions between the reaction vessels. The reagent(s) or probe(s) will be attached only to the hydrophilic regions, that is, the inner wall and the bottom surface of the reaction vessels. The size of each reaction vessel may be less than 1 mm. In this scale, small amounts of sample fluid can overflow large numbers of reaction vessels in 10 seconds, so as to improve sample loading efficiency significantly.

Figure 4:
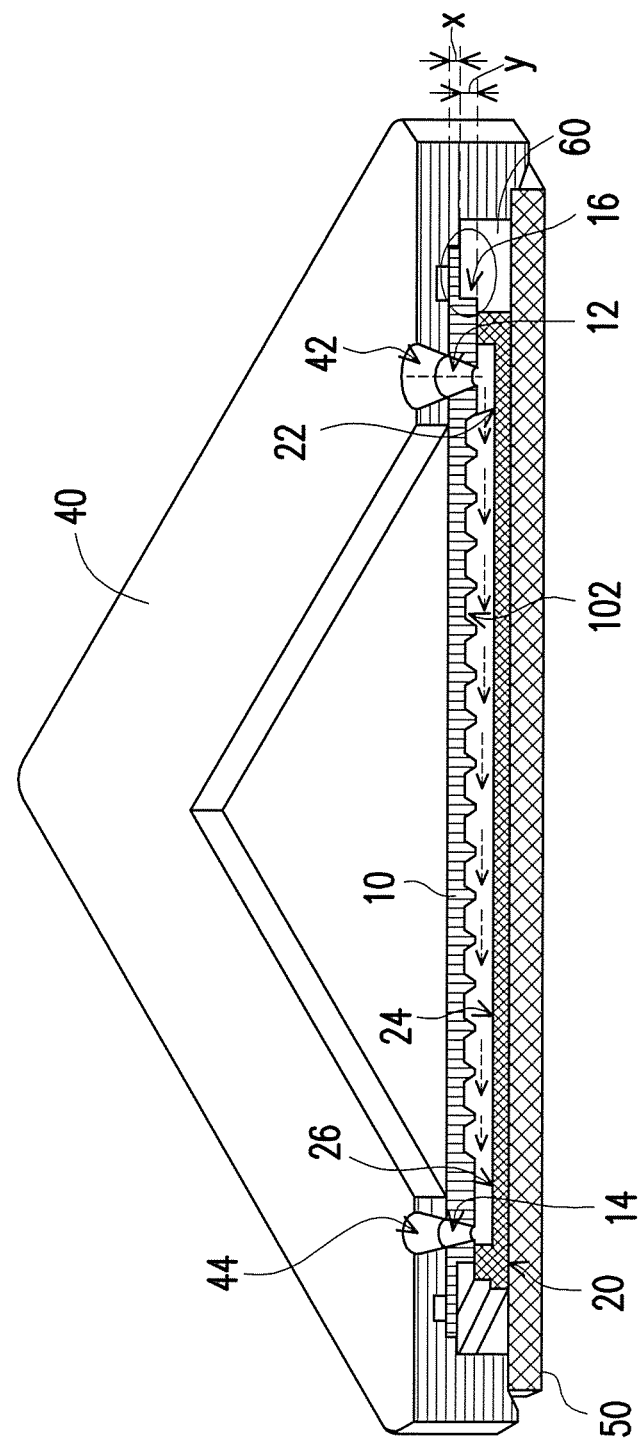
FIG. 4 is a schematic view illustrating a multiplex slide plate device applied in sample solution loading according to the first embodiments of the invention.

FIG. 4 is a schematic view illustrating a multiplex slide plate device applied in sample solution loading according to the first embodiments of the invention. Next, the structure of the multiplex slide plate device in the first embodiment of the invention and its application in sample solution loading will be illustrated in the following descriptions by referring to FIG. 1, FIG. 2 and FIG. 4.

Referring to FIG. 1, the sacrificial layer 20 has a microfluidic channel 28, wherein the microfluidic channel 28 has an injection channel 22, a main channel 24 and a distal channel 26 connected to each other. In the present embodiment, the material of the sacrificial layer 20 may include wax, so the sacrificial layer 20 melts when it is heated to about 60° C. in PCR. However, the invention is not limited thereto, and any material with a melting temperature range of more than room temperature to 60° C. may also be used, and the material with a melting temperature of about 60° C. is preferred. More specifically, the dimension of the sacrificial layer 20 is 37.6 mm×39.6 mm×1.3 mm, for example. The depth of the microfluidic channel 28 is 0.12 mm, for example. The dimension of the main channel 24 is 22.5 mm×22.5 mm, for example.

Referring to FIG. 1 and FIG. 2, the sacrificial layer 20 is assembled to the slide plate 10, wherein the main channel 24 faces the opening portion 102a of reaction vessels 102 in the slide plate 10. Referring to FIG. 1, FIG. 2 and FIG. 4, the sample solution can be injected from the injection hole 12 of the slide plate 10 to the injection channel 22, such that the sample solution flows from the injection channel 22 through the main channel 24 to the distal channel 26, wherein the sample solution loads into each of the reaction vessels 102 of the slide plate 10 while flowing through the main channel 24 (the flowing direction of the sample solution is illustrated by the dashed arrow in FIG. 4).

In FIG. 2, the injection hole 12 and the exhaust hole 14 of the slide plate 10 are arranged in a diagonal line, but the invention is not limited thereto. The arrangement of the injection hole 12 and the exhaust hole 14 can be adjusted according to the arrangement of the injection channel 22 and the distal channel 26 of the sacrificial layer 20, as long as the sample solution is fully extended in the flowing process.

As shown in FIG. 1, the housing 30 may include an upper cover 40 and a bottom plate 50, wherein the upper cover 40 is assembled to the bottom plate 50. More specifically, the dimension of the upper cover 40 is 45 mm×43 mm×5 mm, for example. The dimension of the bottom plate 50 is 42 mm×40 mm×2 mm, for example. In the present embodiment, the upper cover 40 may have a groove to accommodate the slide plate 10 and the sacrificial layer 20, and an injection hole 42 and an exhaust hole 44 may be located in the upper cover 40. However, the structure of housing 30 in the invention is not limited thereto, and any other structure which is able to accommodate the slide plate 10 and the sacrificial layer 20 may also be used. For example, the housing 30 can be an integrally-forming structure, wherein the structure has a tenon to be opened and closed so as to accommodate the slide plate 10 and the sacrificial layer 20. Besides, a guide slot propulsion structure can also be used, such that the slide plate 10 and the sacrificial layer 20 are accommodated in the housing 30.

More specifically, the housing 30 has the thermally conductive effect in PCR. The material of the housing 30 may include a thermally conductive material, wherein the thermally conductive material may be metal such as aluminium and copper, graphite or wafer, but the invention is not limited thereto. In addition, the housing 30 is able to isolate the slide plate 10 and the sacrificial layer 20 from the external environment, so as to avoid the reaction from being affected.

In the present embodiment, the housing 30 may include a label (not illustrated). When the multiplex slide plate device of the invention is applied to an apparatus (for example, thermal cycling PCR apparatus) with label reading device, the label reading device can read the label on the housing 30. The label may be a handwriting label, barcode or other kind of labels, but the invention is not limited thereto, and suitable labels can be selected according to the requirements and the label reading device.

Referring to FIG. 1, FIG. 2 and FIG. 4, the sample solution can be injected from the injection hole 42 of the housing 30 and the injection hole 12 of the slide plate 10 to the injection channel 22, such that the sample solution flows from the injection channel 22 through the main channel 24 to the distal channel 26, wherein the sample solutions loads into each of the reaction vessels 102 of the slide plate 10 while flowing through the main channel 24 (the flowing direction of the sample solution is illustrated by the dashed arrow in FIG. 4). Besides, as shown in FIG. 4, the slide plate 10 may further include a double-step structure 16 at the edge thereof. A space 60 is formed between the double-step structure 16, the sacrificial layer 20, the upper cover 40 and the bottom plate 50, and the space 60 has an effect of avoiding bubble generation. In the present embodiment, double-step structure 16 may have a first step x and a second step y, wherein the thickness ratio of the first step x and the second step y is 1:1, and the thickness of the first step x and the second step y is respectively 1 mm and the total thickness 2 mm, for example.

In FIG. 1, the injection hole 42 and the exhaust hole 44 of the upper cover 40 are arranged in a diagonal line, but the invention is not limited thereto. The arrangement of the injection hole 42 and the exhaust hole 44 depends on the arrangement of the injection hole 12 and the exhaust hole 14 of the slide plate 10. In other ords, it can be adjusted according to the arrangement of the injection channel 22 and the distal channel 26 of the sacrificial layer 20, as long as the sample solution is fully extended in the flowing process.

Figure 5:
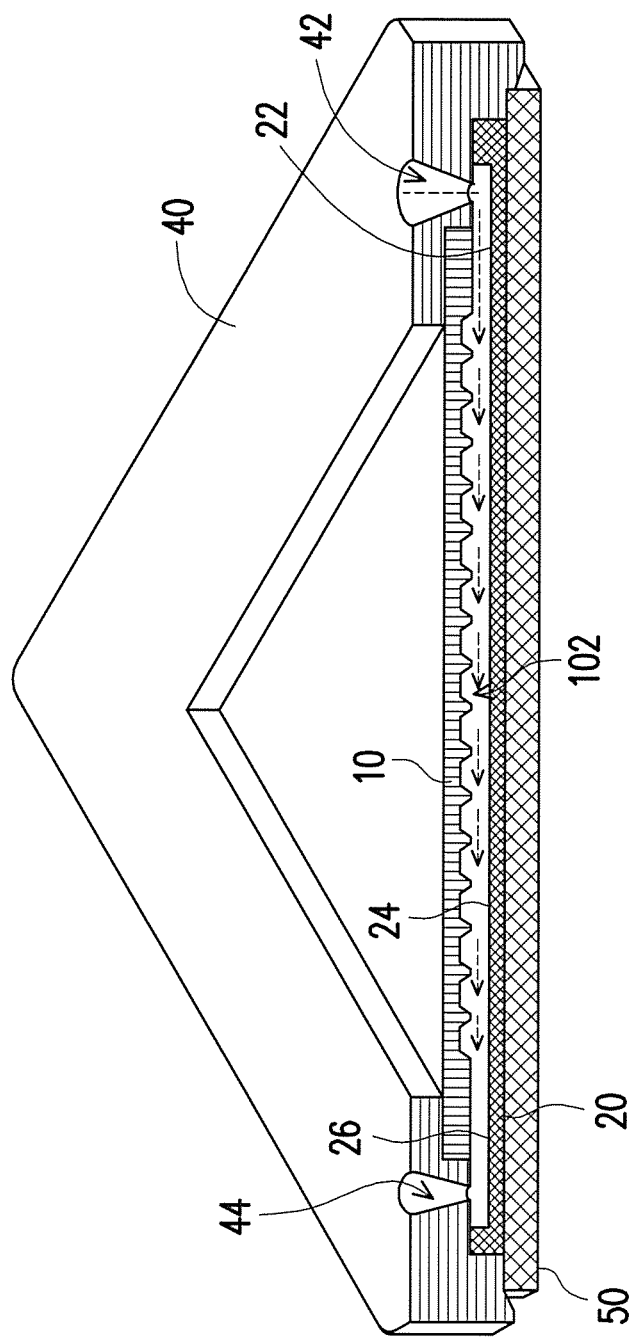
FIG. 5 is a schematic view illustrating a multiplex slide plate device applied in sample solution loading according to the second embodiments of the invention.

FIG. 5 is a schematic view illustrating a multiplex slide plate device applied in sample solution loading according to the second embodiments of the invention. The second embodiment illustrated in FIG. 5 is similar to the first embodiment illustrated in FIG. 1, FIG. 2, FIG. 3 and FIG. 4, so the same reference number refers to the same component, and relevant descriptions are not repeated herein.

The difference between the present embodiment and the aforementioned first embodiment is that, the slide plate 10 does not have the injection hole 12 and the exhaust hole 14, and the slide plate 10 does not have the double-step structure 16 at the edge. Besides, the dimension of the sacrificial layer 20 is larger than the dimension of the slide plate 10. For example, the dimension of the slide plate 10 in the present embodiment may be the same as the dimension of the slide plate 10 in the aforementioned first embodiment, but the dimension of the main channel 24 in the sacrificial layer 20 may be more than 22.5 mm×22.5 mm, for example.

Referring to FIG. 5, the sample solution can be injected from the injection hole 42 of the housing 30 to the injection channel 22, such that the sample solution flows from the injection channel 22 through the main chancel 24 to the distal channel 26, wherein the sample solution loads in to each of the reaction vessels 102 of the slide plate 10 while flowing through the main channel 24 (the flowing direction of the sample solution is illustrated by the dashed arrow in FIG. 5).

Figure 6A:
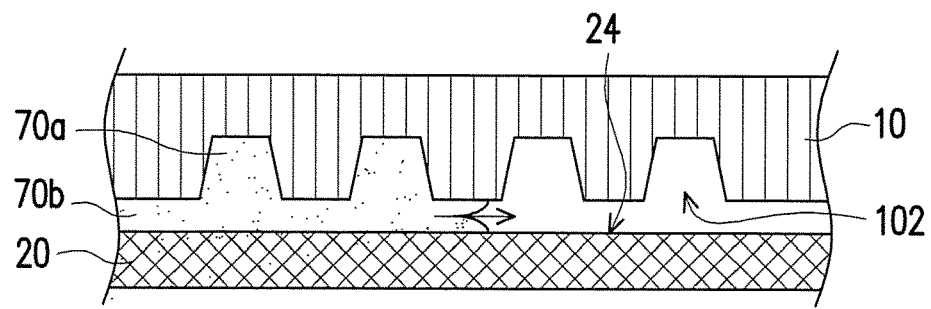
FIG. 6A to FIG. 6C are schematic views illustrating an operation method of a multiplex slide plate device of the invention.
Figure 6B:
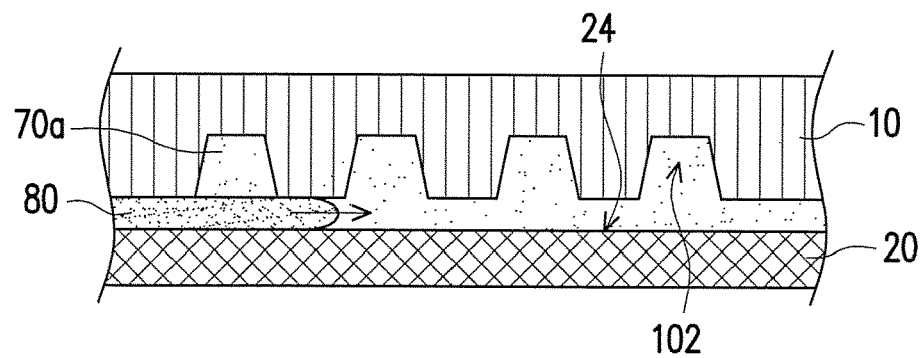
Figure 6C:
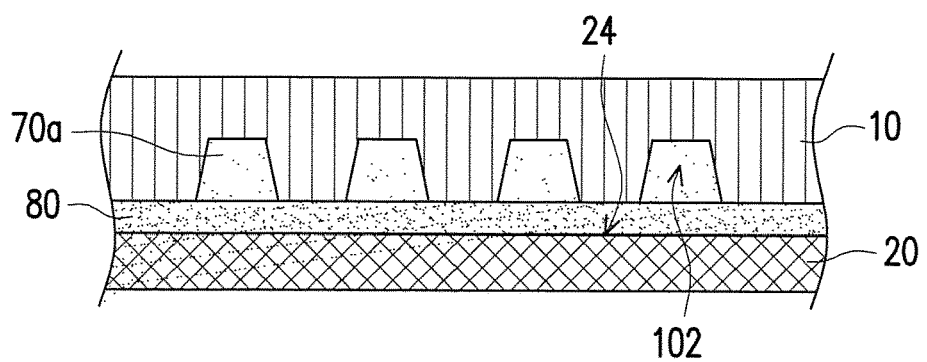

The invention further provides an operation method of the multiplex slide plate device illustrated in the aforementioned first embodiment and second embodiment. FIG. 6A to FIG. 6C are schematic views illustrating an operation method of a multiplex slide plate device of the invention. Next, the operation method of the multiplex slide plate device of the invention is illustrated in the following descriptions by referring to FIG. 6A to FIG. 6C. It should be noted that the details of multiplex slide plate device structure and sample solution loading are illustrated in the foregoing descriptions, and are therefore not repeated herein.

First, the multiplex slide plate device is assembled. The assembled multiplex slide plate device is fixed and sealed by adhesive dripping, for example, so as to maintain the airtight condition and avoid the sample solution from flowing outwards.

Next, the sample solution is injected from the injection hole of the housing to the injection channel by pipetting operation or other suitable liquid dispenser, such that the sample solution flows from the injection channel through the main channel to the distal channel. As shown in FIG. 6A, the sample solution 70a and 70b loads into each of the reaction vessels 102 while flowing through the main channel 24. More specifically, the total input amount of the sample solution is 60 µl, for example.

Afterwards, the oil is injected from the injection hole of the housing to the injection channel, such that the oil flows from the injection channel through the main channel to the distal channel. As shown in FIG. 6B to FIG. 6C, the oil 80 removes the sample solution 70b which is not loaded into the reaction vessels 102 while flowing through the main channel 24. More specifically, the oil is mineral oil or silicone oil, for example.

Finally, in the PCR experiment process, the sacrificial layer is heated to melt, and the melted sacrificial layer mixes with the oil, wherein the melting temperature of the sacrificial layer may be about 60° C. It should be noted that the distance between the slide plate and the sacrificial layer of the invention is at least about 10 µm (for example, 10 µm to 50 µm), and the sacrificial layer has a certain thickness (for example, 550 µm to 590 µm). Therefore, when the melted sacrificial layer mixes with the oil, the distance between the slide plate and the bottom plate is about 600 µm, so the reaction can be performed successfully. A certain distance between the slide plate and the bottom plate can be maintained without adding an excess amount of sample, so it is able to save the input amount of sample.

Based on the above, the invention provides a multiplex slide plate device and an operation method thereof suitable for molecular biological detection, such that the sample can be loaded into each reaction vessel of the slide plate quickly and uniformly while flowing through the main chaimel of the sacrificial layer, and then the sample solution which is not loaded into the reaction vessels is removed by the oil. Therefore, all of the reaction vessels can be filled in an extremely short time by single pipetting operation, so the experiment operation can be simplified with time-saving effect. In addition, a certain distance between the slide plate and the bottom plate can be maintained without adding an excess amount of sample, so it is able to save the input amount of sample.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A multiplex slide plate device, comprising:
   a transparent slide plate comprising polycarbonate or polymethyl methacrylate, and having a plurality of reaction vessels, wherein the reaction vessels are arranged in an array, and each of the reaction vessels has an opening portion and a bottom portion; and
   a microfluidic channel formed between a wax sacrificial layer and the transparent slide plate, wherein the microfluidic channel has an injection channel, a main channel and a distal channel connected to each other, and the wax sacrificial layer is assembled to the transparent slide plate, wherein the main channel faces the opening portion.

2. The multiplex slide plate device of claim 1, further comprising a housing which accommodates the transparent slide plate and the wax sacrificial layer, and the housing has an injection hole and an exhaust hole.

3. The multiplex slide plate device of claim 2, wherein a material of the housing comprises a thermally conductive material.

4. The multiplex slide plate device of claim 2, wherein the housing comprises an upper cover and a bottom plate, the upper cover is assembled to the bottom plate, and the upper cover has a groove to accommodate the transparent slide plate and the wax sacrificial layer, the injection hole and the exhaust hole are located in the upper cover.

5. The multiplex slide plate device of claim 2, wherein the housing comprises a label.

* * * * *